United States Patent
Holman et al.

(10) Patent No.: US 12,233,283 B2
(45) Date of Patent: Feb. 25, 2025

(54) INTRAORAL POSITIONING DEVICE

(71) Applicant: Radtec Medical Devices, Inc., San Carlos, CA (US)

(72) Inventors: Ross Holman, Menlo Park, CA (US); Brian Knott, Palo Alto, CA (US)

(*) Notice: Subject to any disclaimer, the term of this patent is extended or adjusted under 35 U.S.C. 154(b) by 0 days.

(21) Appl. No.: 18/070,397

(22) Filed: Nov. 28, 2022

(65) Prior Publication Data
US 2023/0226373 A1 Jul. 20, 2023

Related U.S. Application Data

(63) Continuation of application No. 16/479,908, filed as application No. PCT/US2018/015201 on Jan. 25, 2018, now abandoned.

(60) Provisional application No. 62/451,766, filed on Jan. 29, 2017.

(51) Int. Cl.
*A61N 5/10* (2006.01)
*A61B 13/00* (2006.01)
*A61B 90/16* (2016.01)
*A61B 6/04* (2006.01)

(52) U.S. Cl.
CPC .............. *A61N 5/10* (2013.01); *A61B 13/00* (2013.01); *A61B 90/16* (2016.02); *A61N 5/103* (2013.01); *A61B 6/04* (2013.01); *A61N 5/1045* (2013.01); *A61N 2005/1097* (2013.01)

(58) Field of Classification Search
CPC .... A61N 5/10–1084; A61N 2005/1085–1098; A61B 90/16
See application file for complete search history.

(56) References Cited

U.S. PATENT DOCUMENTS

| | | |
|---|---|---|
| 6,244,865 B1 | 6/2001 | Nelson et al. |
| 8,002,465 B2 | 8/2011 | Ahn |
| 9,629,972 B1 | 4/2017 | Vu |
| 9,937,019 B1 | 4/2018 | Copps |
| 2001/0047805 A1 | 12/2001 | Scarberry et al. |
| 2002/0139375 A1 | 10/2002 | Kulick |
| 2004/0033468 A1 | 2/2004 | Fischer et al. |
| 2008/0255498 A1 | 10/2008 | Houle |
| 2009/0050161 A1 | 2/2009 | Burdumy |
| 2011/0126840 A1 | 6/2011 | Ogilvie et al. |

(Continued)

OTHER PUBLICATIONS

Patent Cooperation Treaty, Written Opinion an International Search Report issued in PCT/US2018;015201, Mar. 9, 2018, pp. 1-12.

*Primary Examiner* — Thaddeus B Cox
(74) *Attorney, Agent, or Firm* — Pillsbury Winthrop Shaw Pittman LLP (57) ABSTRACT

An intraoral positioning device (IPD) is disclosed for positioning in a patient's mouth for radiation therapy planning and treatment, the device comprising an engagement member configured to engage structure within a patient's mouth during radiation planning or treatment, wherein the engagement member includes an upper wall, a lower wall and first and second side walls extending from and between the upper and lower walls, whereby the upper, lower and first and second side walls form top, bottom, front and rear walls of a bite block, and a handle extending from the engagement member to enable a user to grasp the IPD for introducing and removing it from the patient's mouth.

12 Claims, 7 Drawing Sheets

(56) References Cited

U.S. PATENT DOCUMENTS

| | | | |
|---|---|---|---|
| 2012/0012120 A1* | 1/2012 | Giffey | A61B 13/00 128/859 |
| 2014/0053851 A1 | 2/2014 | Podmore | |
| 2014/0072932 A1 | 3/2014 | Brawn et al. | |
| 2014/0287379 A1 | 9/2014 | Chun et al. | |
| 2016/0095995 A1* | 4/2016 | Haider | A61M 16/0493 128/207.14 |

* cited by examiner

FIG. 35 ously
INTRAORAL POSITIONING DEVICE

REFERENCE TO RELATED APPLICATIONS

This application is a continuation of U.S. patent application Ser. No. 16/479,908, filed Jul. 22, 2019, and which is a U.S. National Stage of PCT Serial No. PCT/US18/15201, filed Jan. 25, 2018, which claims priority to U.S. provisional application No. 62/451,766, filed on Jan. 29, 2017 entitled "Intraoral Positioning Device," all of the aforementioned which are incorporated by reference herein in their entirety.

FIELD OF THE INVENTION

The present invention relates and intraoral positioning device.

BACKGROUND OF THE INVENTION

Over the last 10 years, head and neck cancer diagnoses have increased annually by ten to fifteen percent. The rise in occurrence is largely the result of the increase in HPV infections. Radiation therapy (e.g. Intensity modulated radiation therapy treatment, IMRT, or intensity modulated proton therapy, IMPT) is a primary treatment modality along with surgery, and chemotherapy for such cancers. In IMRT and IMPT, patient target locations are treated with small beams of high intensity radiation that are delivered from multiple directions to conform to the shape of the tumor while avoiding healthy anatomic structures to reduce radiation exposure. In order for radiation therapy to be effective, i.e., to reduce or remove malignant tumors, the patient must remain in position and motionless during many repeatable treatment sessions (e.g. 30). Prior devices for IMRT treatments, however, have been less than effective for such purposes when it comes to positioning the dental structures (e.g., lower jaw) including the tongue. This is due to the inadequacy of prior products used to make such devices.

SUMMARY OF THE INVENTION

Embodiments of an intraoral positing device are disclosed.

In accordance with an embodiment of this disclosure, an intraoral positioning device (IPD) is disclosed for positioning in a patient's mouth for radiation therapy planning and treatment, the device comprising: an engagement member configured to engage structure within a patient's mouth during radiation planning and/or treatment, wherein the engagement member includes an upper section, a lower section and middle section extending from and between the upper and lower sections, whereby the upper, middle and lower sections together form walls of a bite block and define an opening for receiving and positioning a tongue of the patient; and a handle extending from the engagement member to enable a user to grasp the IPD for introducing and removing it from the patient's mouth.

In accordance with another embodiment of this disclosure, an intraoral positioning device (IPD) is disclosed for positioning in a patient's mouth for radiation therapy planning and treatment, the device comprising: an engagement member configured to engage structure within a patient's mouth during radiation planning or treatment, wherein the engagement member includes an upper wall, a lower wall and a first side wall extending from and between the upper and lower walls, whereby the upper, lower and first side wall form the top, bottom and rear walls of a bite block, respectively.

In accordance with another embodiment of the disclosure, an intraoral positioning device (IPD) is disclosed for positioning in a patient's mouth for radiation therapy planning and treatment, the device comprising: an engagement member configured to engage structure within a patient's mouth during radiation planning or treatment, wherein the engagement member includes an upper wall, a lower wall and first and second side walls extending from and between the upper and lower sections, whereby the upper, lower and first and second side walls form top, bottom, front and rear walls of a bite block; and a handle extending from the engagement member to enable a user to grasp the IPD for introducing and removing it from the patient's mouth.

DETAILED DESCRIPTION OF THE INVENTION

Embodiments of the present invention are described herein with reference to the drawing figures. FIGS. 1-7 depict various views of example intraoral positioning device (IPD) 100 that is used to position a patient's (user's) jaw, mouth and soft tissue (e.g., tongue) for intensity-modulated radiation therapy (IMRT) planning and treatment). IPD 100 is a device that positions oral structures and displaces soft tissue (thereby sparing such tissue unnecessary exposure to radiation) by creating separation between a patient's anatomical structures (e.g., the patient's upper and lower arches). In addition, IPD 100 may also be used for other planning and treatment procedures involving radiation therapy including for example intensity modulated proton therapy—IMPT, CT imaging, X-ray imaging and MRI imaging. IPD 100 is configured or manufactured as one-piece (integral), but those skilled in the art know that IPD 100 may be made in two or more pieces that are combined to form IPD 100.

As shown, IPD 100 comprises an engagement member 101 that is configured to engage anatomical structures in a patient's mouth including tissue, tongue and/or teeth as described below. Specifically, engagement member 101 includes upper section 102, middle section 104 and lower section 106. Upper section 102 is an arc shaped wall of a single diameter that includes an annular indentation or channel 102*a* (as a positioning aid) positioned toward the rear of upper section 102 for the maxilla or teeth to engage. Channel 102*a* is defined by a single curved wall that is configured into a trough or groove. However, channel 102*a* may be defined by two, three or more walls that create the groove. A wall may be linear or rounded to a degree. For example, channel 102*a* may be configured as a rectangular groove.

Upper section 102 alternatively may incorporate other positioning aids to create positive engagement of the maxilla or upper teeth. However, upper section 102 may be configured without any indention or channel for a patient who is denture-less. Channel 102*a* is one form of a positioning aid. Other possible positioning aids may include channels, grooves, indentations, recessions, thermo-molded pieces or other structures, sections or positioning aids known to those skilled in the arts. Middle section 104 is configured as a wall that is vertically positioned in the rear (defining the opening or cavity as described below). Lower section 106 is configured as a flat wall. However, those skilled in the art know that the upper, middle and/or lower section may be configured to any shape or size to achieve desired results as known to those skilled in the art.)

Upper section 102, middle section 104 and lower section 106 (i.e., these walls) together form a bite block and define an opening 108 (cavity) for receiving and positioning a tongue. As part of bite block configuration, middle section 104 extends vertically from and functions as a back/rear wall between upper and lower sections or walls 102 and 106 that define opening 108. The opening 108 or cavity enables a patient's tongue to be extended forward over the lower incisor and within IPD 100. Upper section 102 extends beyond the length of lower section 106 as shown (similar to an awning or overhang). This extended portion 102*b* acts as a displacement stent for the tongue, thereby limiting movement of the patient's tongue. The stent (overhang or extended portion 102*b*) is configured as an arc (curved shape) as shown in FIGS. 1-6, but the stent may be configured in any other shape to achieve desired results as known to those skilled in the art. In this example in FIGS. 1-6, tongue displacement stent 102*b* acts a ceiling, thereby preventing a patient's tongue from rising (i.e., moving vertically) above. The opening 108 (cavity) in the structure may also be configured in various shapes and sizes to accommodate the size of different patient (user) anatomic structures. Larger mouths generally have larger tongues as well.

Upper section 102, middle section 104 and/or lower section 106 may incorporate additional positioning aids or elements to create positive engagement of the mandible and associated dental structures. These positioning aids may include channels, grooves, indentations or recessions, thermo-molded pieces or sections, and other positioning aids known to those skilled in the arts.

IPD 100 also includes handle or bar 110 extending from middle section or wall 104, axially with respect to engagement member 101, to enable a user to grasp IPD 100. Handle 110 may have various shapes to achieve desired results. Handle 110 may incorporate ladder steps or ledges to add in grasping. Alternatively, handle 110 may be fully open, solid or any other configuration to achieve desired results.

FIGS. 7-12 depict views of another example IPD 700 (intraoral positioning device). IPD 700 is similar to IPD 100 in that IPD 700 comprises an engagement member 701 that is configured to engage a patient's anatomical structures (e.g., tissue, tongue and teeth). Specifically, engagement member 701 includes an upper section or wall comprising segments 702*a*, 702*b*, 702*c* (described below), middle section or wall 704 and lower section or wall 706.

As mentioned, in this example, upper section is divided into three segments: inner segment 702*a*, outer segment 702*b* and transition segment 702*c*. Both inner and outer segments 702*a* and 702*b* are configured as arc or concave shape, but having different diameters from one another. In this example, segment 702*a* has a larger diameter than segment 702*b*. Segment 702*a* transitions into segment 702*b* gradually through a transition segment or section 702*c*. That is, segment section 702*c* functions as a transition between inner segment 702*a* and outer segment 702*b*, and transition segment is shown (e.g., FIG. 10) as a curve wall, in reverse to the curvature of upper section 702*a*, with a gradually decreasing diameter, thereby transitioning between inner and outer segments. However, those skilled in the art know that any number of segments (curved or linear) may be used to achieve desired results. Segment 702*b* extends outwardly from segment 702*a* via segment 702*c*.

Segment 702*a* includes an annular indentation or channel 702*a*1 (as a positioning aid) positioned toward the rear of upper section 702 for the maxilla or teeth to engage as described above. As described above, channel 702*a*1 is defined by a single wall that is configured as a trough. However, channel 702*a*1 may be defined by two, three or more segments or walls that create a groove or other engagement point. A wall may be linear or rounded to a degree. For example, channel 702*a*1 may be configured as a rectangular groove.

As described above, upper section alternatively may incorporate other positioning aids to create positive engagement of the maxilla or upper teeth. However, upper section 702 may be configured without any indention or channel for a patient who is denture-less. Channel 702a1 is one form of a positioning aid. Other possible positioning aids may include channels, grooves, indentations, recessions, thermo-molded pieces or other structures, sections or positioning aids known to those skilled in the arts.

Similar to middle section 104 above, middle section 704 is configured as a wall that is vertically positioned in the rear (defining the opening or cavity as described below). Lower section 706 is configured as a flat wall. However, those skilled in the art know that the upper, middle and/or lower section may be configured to any shape or size to achieve desired results as known to those skilled in the art.)

Segment 702a of the upper section, middle section 704 and lower section 706 (i.e., these walls) together form a bite block and define an opening 708 (cavity) for receiving and positioning a tongue. Segment 702b of upper section 702 extends beyond the length of lower section 706 as shown. This extended portion 702b acts as a displacement stent for the tongue, thereby limiting movement of the patient's tongue. The stent (extended portion 702b) is configured as an arc (curved shape) as shown in FIGS. 7-12, but the stent may be configured in any other shape to achieve desired results as known to those skilled in the art. In this example, tongue displacement stent 702b acts a ceiling, thereby preventing a patient's tongue from rising (i.e., moving vertically) above. The opening 708 (cavity) in the structure may also be configured in various shapes and sizes to accommodate the size of different patient (user) anatomic structures. Larger mouths generally have larger tongues as well.

Upper section 702, middle section 704 and/or lower section 706 may incorporate additional positioning aids or elements to create positive engagement of the mandible and associated dental structures. These positioning aids may include channels, grooves, indentations or recessions, thermo-molded pieces or sections, and other positioning aids known to those skilled in the arts.

IPD 700 also includes handle or bar 710 extending from middle section 704 to enable a user to grasp IPD 700. Handle 710 may have various shapes to achieve desired results. Handle 710 may incorporate ladder steps or ledges to add in grasping. Alternatively, handle 710 may be open, solid or any other configuration to achieve desired results.

FIG. 13-18 depict views of another example IPD 1300 (intraoral positioning device). This IPD 1300 is similar to IPD 700 in FIGS. 7-12. IPD 1300 comprises an engagement member 1301 that incorporates an upper section 1302 with an inner segment 1302a, lower segment 1302b and transition segment or section 1302c.

Figure 1:
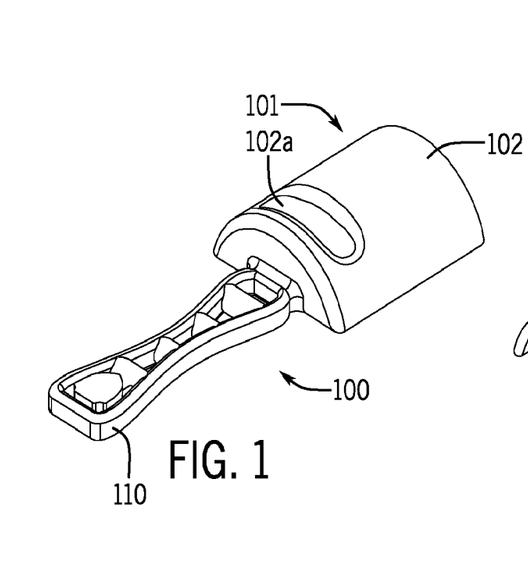
FIG. 1 depicts a rear perspective view of an example intraoral positioning device (IPD).
Figure 2:
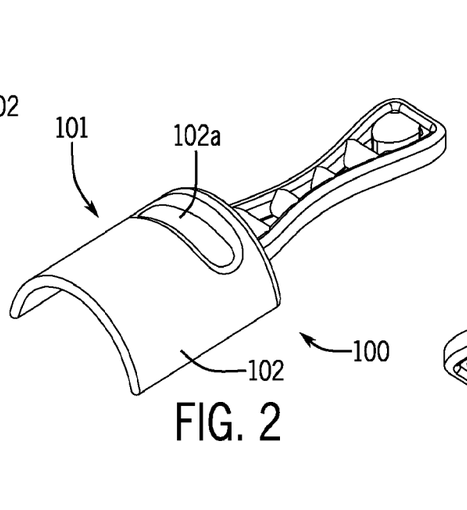
FIG. 2 depicts a front perspective view of the IPD in FIG. 1.
Figure 3:
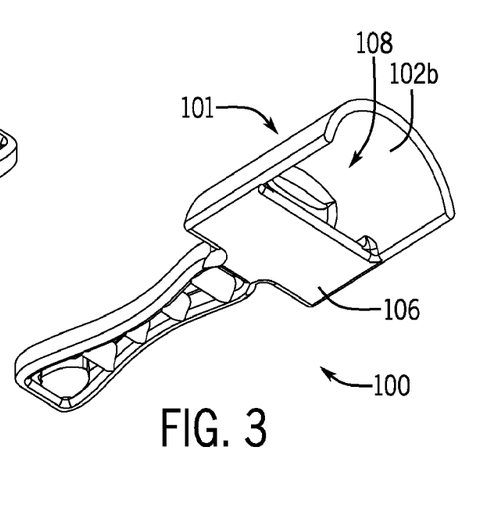
FIG. 3 depicts a bottom perspective view of the IPD in FIG. 1.
Figure 4:
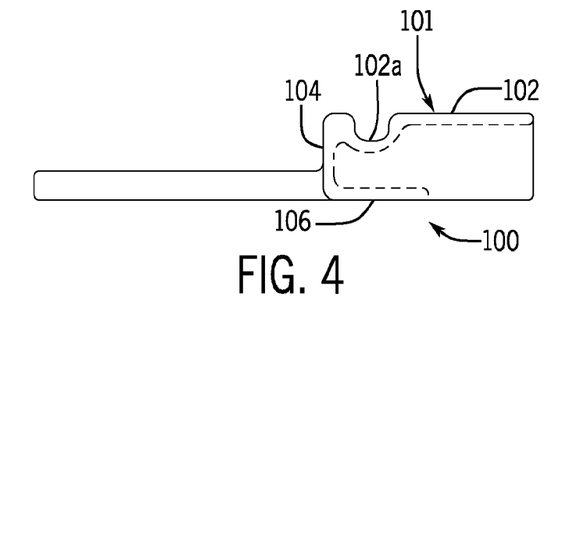
FIG. 4 depicts a side view of the IPD in FIG. 1.
Figures 5, 6:
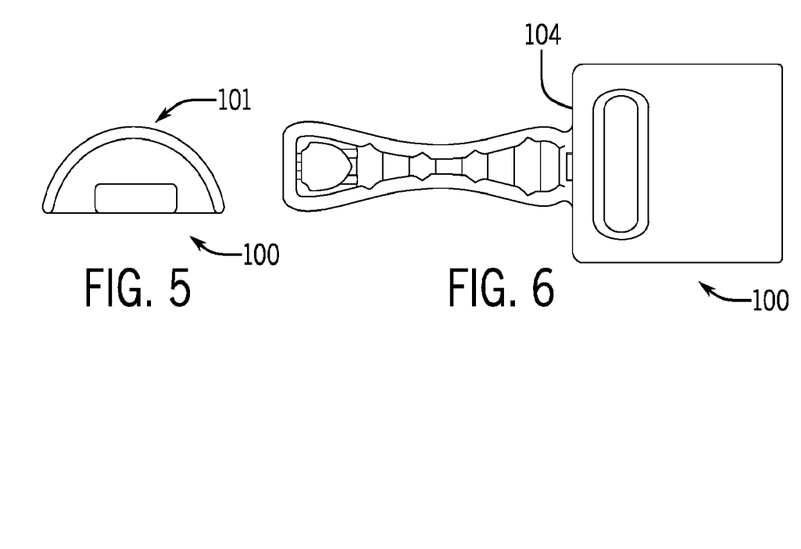
FIG. 5 depicts a front view of the IPD in FIG. 1.
FIG. 6 depicts a top view of the IPD in FIG. 1.
Figure 7:
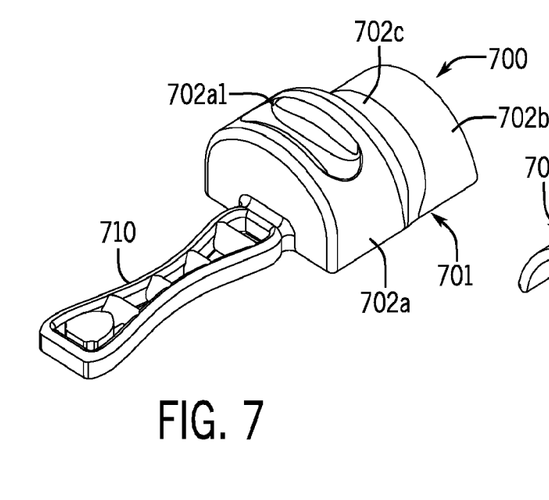
FIG. 7 depicts a rear perspective view of another example IPD.
Figure 8:
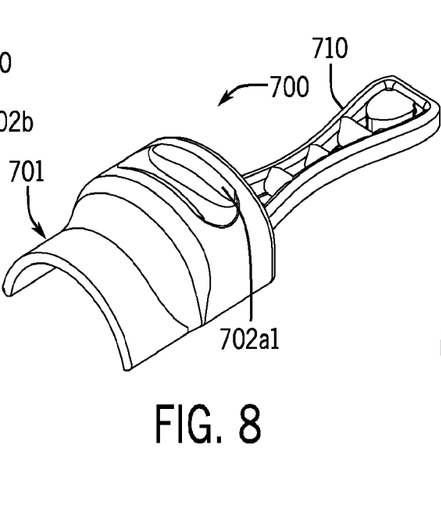
FIG. 8 depicts a front perspective view of the IPD in FIG. 7.
Figure 9:
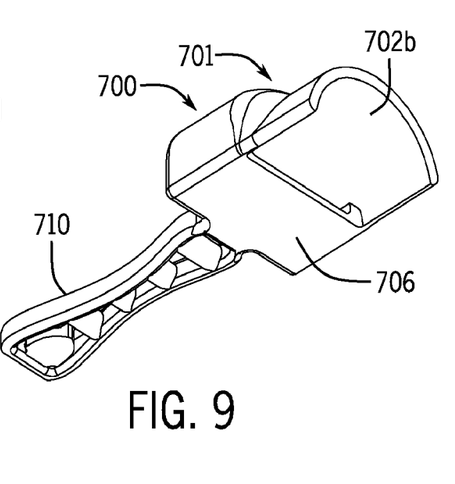
FIG. 9 depicts a bottom perspective view of the IPD in FIG. 7.
Figure 10:
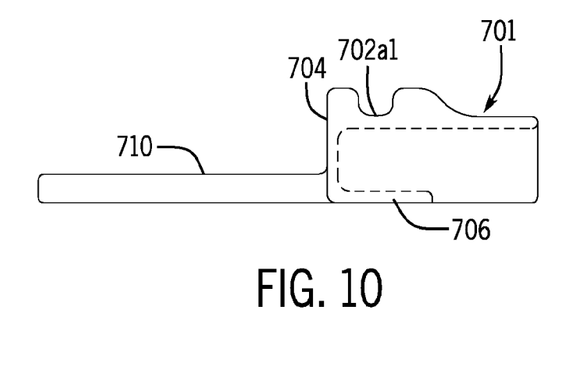
FIG. 10 depicts a side view of the IPD in FIG. 7.
Figure 11:
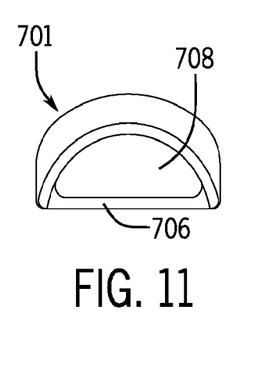
FIG. 11 depicts a front view of the IPD in FIG. 7.
Figure 12:
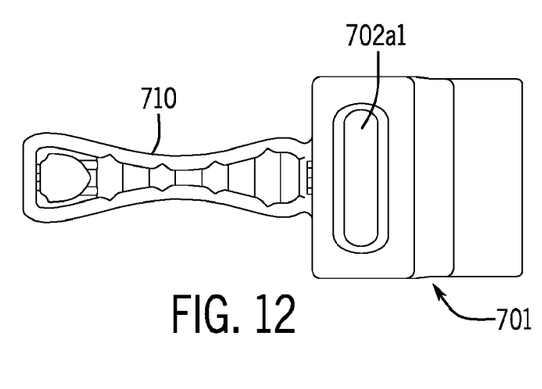
FIG. 12 depicts a top view of the IPD in FIG. 7.
Figures 13, 14:
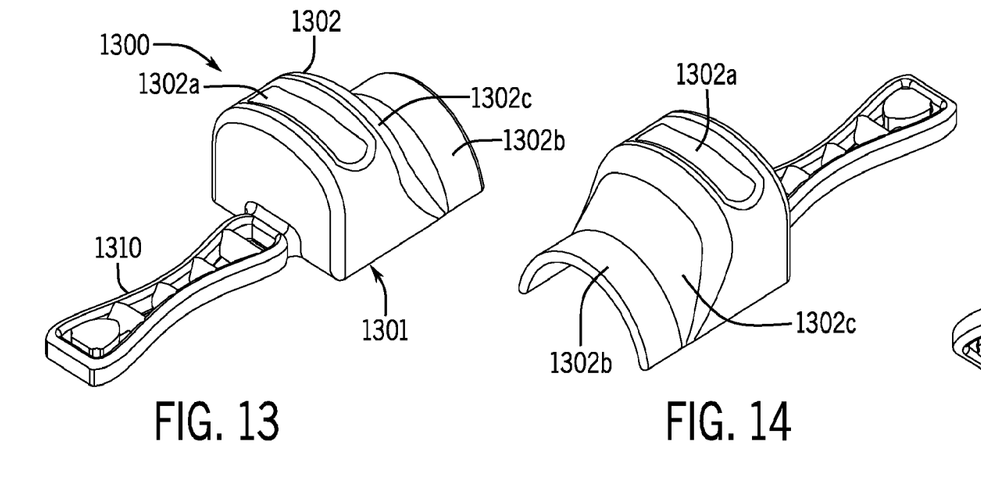
FIG. 13 depicts a rear perspective view of another example IPD.
FIG. 14 depicts a front perspective view of the IPD in FIG. 13.
Figure 15:
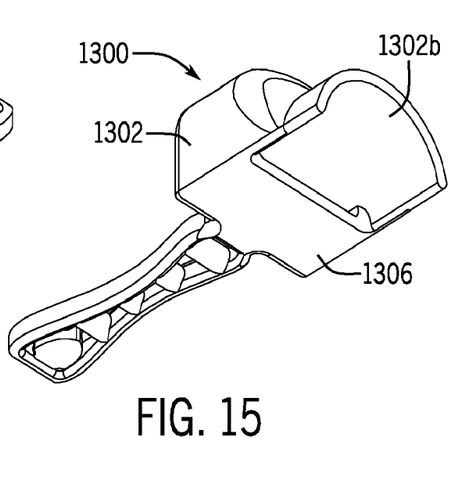
FIG. 15 depicts a bottom perspective view of the IPD in FIG. 13.
Figure 16:
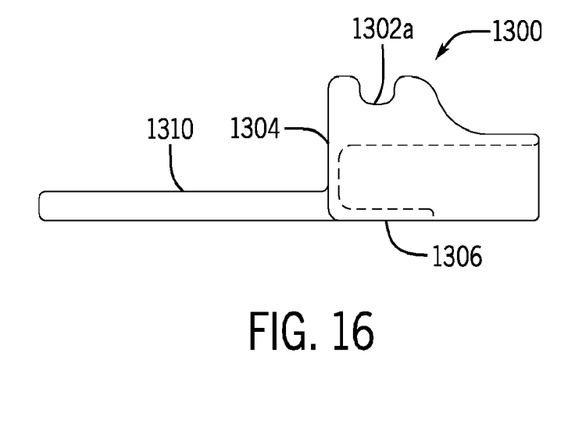
FIG. 16 depicts a side view of the IPD in FIG. 13.
Figure 17:
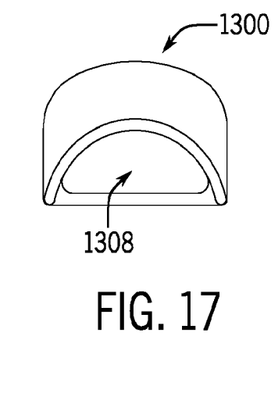
FIG. 17 depicts a front view of the IPD in FIG. 13.
Figure 18:
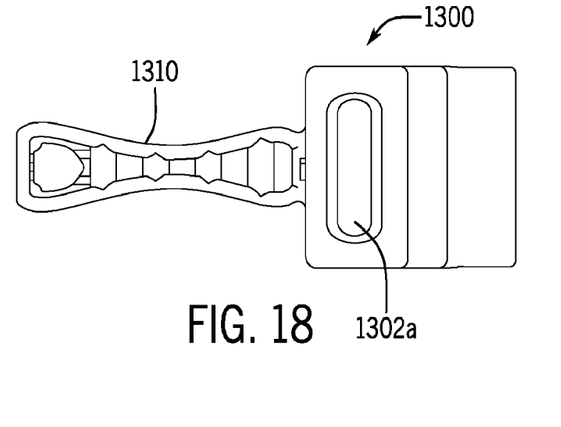
FIG. 18 depicts a top view of the IPD in FIG. 13.
Figure 19:
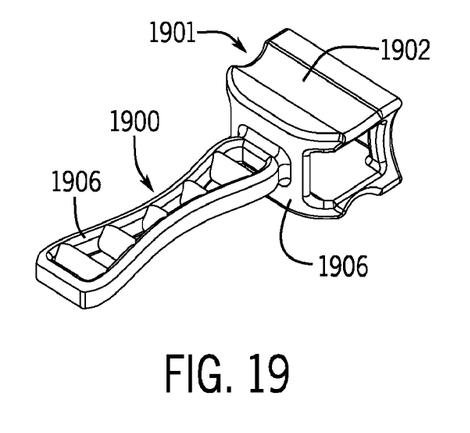
FIG. 19 depicts a rear perspective view of another example IPD.
Figure 20:
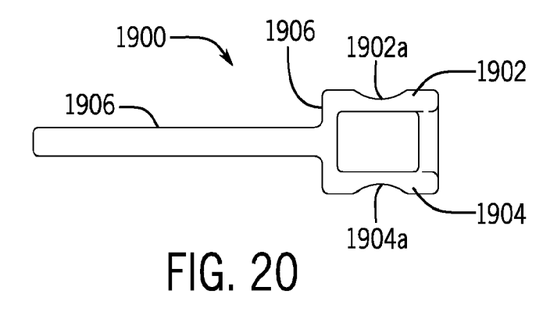
FIG. 20 depicts a side view of the IPD in FIG. 19.
Figure 21:
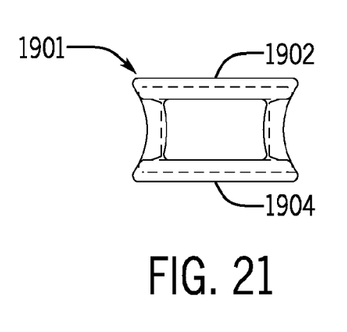
FIG. 21 depicts a front view of the IPD in FIG. 19.
Figure 22:
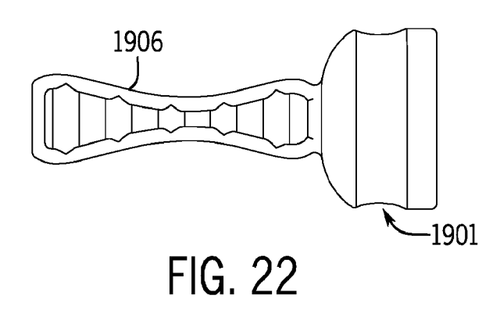
FIG. 22 depicts a top view of the IPD in FIG. 19.
Figure 23:
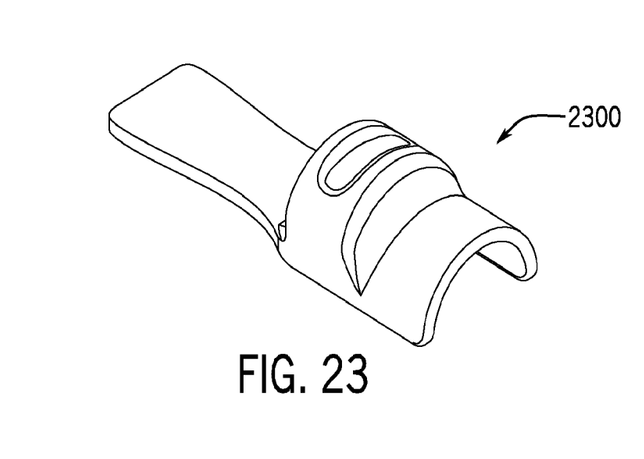
FIG. 23 depicts a front perspective view of another example IPD.
Figure 24:
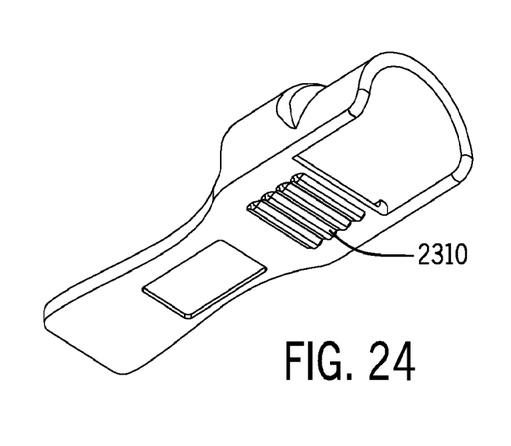
FIG. 24 depicts a bottom perspective view of the IPD in FIG. 23.
Figure 25:
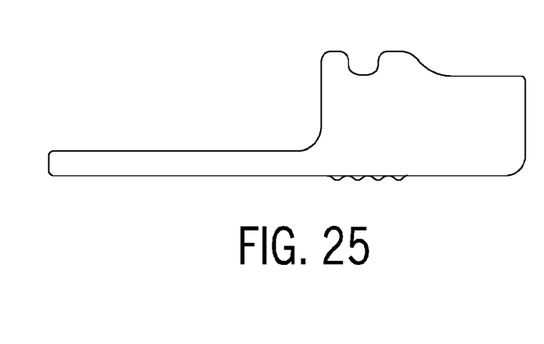
FIG. 25 depicts a side view of the IPD in FIG. 23.
Figure 26:
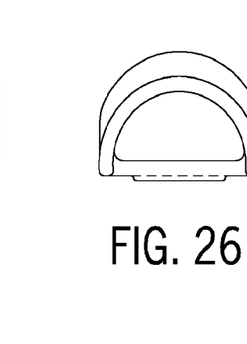
FIG. 26 depicts a front view of the IPD in FIG. 23.
Figure 27:
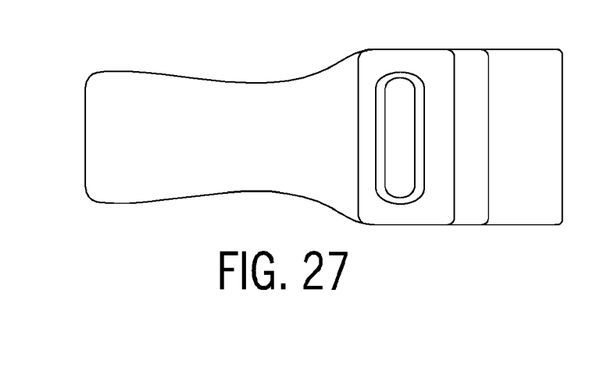
FIG. 27 depicts a top view of the IPD in FIG. 23.
Figure 28:
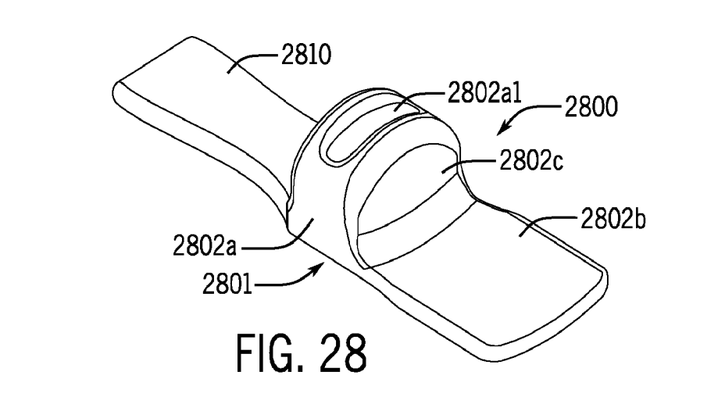
FIG. 28 depicts a front perspective view of another example IPD.
Figure 29:
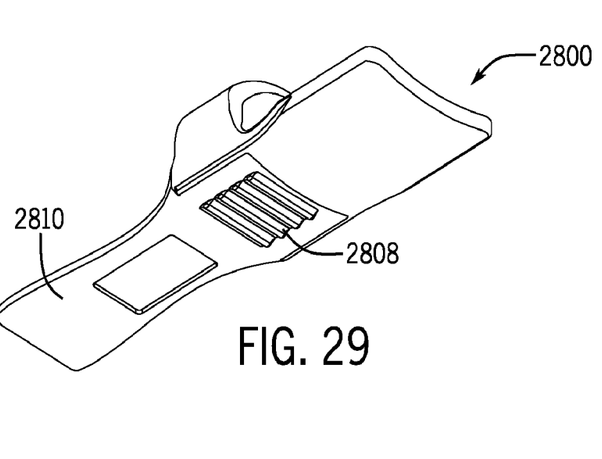
FIG. 29 depicts a bottom perspective view of the IPD in FIG. 28.
Figure 30:
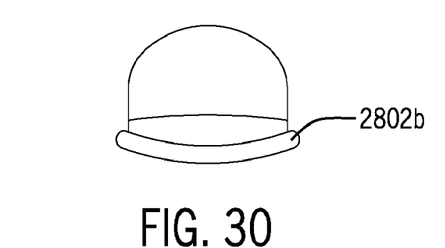
FIG. 30 depicts a front view of the IPD in FIG. 28.
Figure 31:
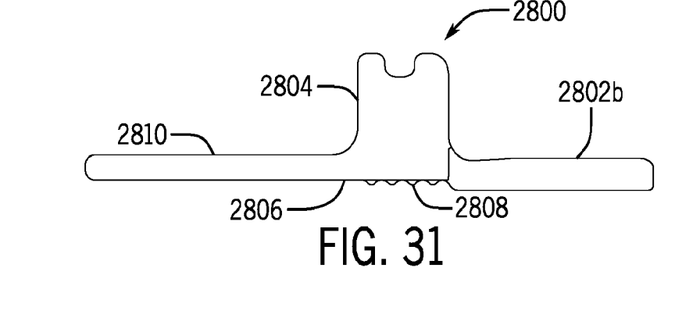
FIG. 31 depicts a side view of the IPD in FIG. 28.
Figure 32:
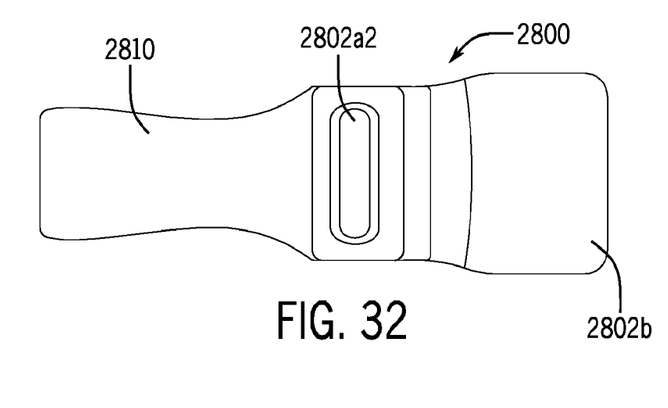
FIG. 32 depicts a top view of the IPD in FIG. 28.

The diameter of the inner segment 1302a of the upper section 1302 is significantly greater than lower segment 1302b. Therefore, the transition segment 1302c transitions at a greater slope than the transition segment shown in FIGS. 7-12. FIG. 16 depicts this clearly. IPD 1300 includes a middle section or wall 1304 and lower section or wall 1306. Upper section 1302, middle section 1304 and lower section 1306 (i.e., these walls) together form a bite block and define an opening 1308 (cavity) for receiving and positioning a tongue similar to the example in FIGS. 1-6 above. IPD 1300 further includes handle 1310 for grasping as described above.

In short, as seen in FIGS. 13-18, example IPD 1300 varies in overall sizing and form from the example IPD 100 in FIGS. 1-6, but functions similarly to the example in FIGS. 1-6.

FIGS. 19-22 depict views of another example intraoral positioning device 1900. As shown, the bite block of the IPD 1900 has upper and lower sections or walls 1902, 1904 and middle wall 1906 extending from and between upper and lower walls 192, 1904. Upper wall 1902, lower wall 1904 and middle wall 1906 together define the bite block of IPD 1900 having and opening to receive a patient's tongue. However, IPD 1900 does not include vertical side sections or walls or an extended tongue displacement stent as shown in the other examples. Upper and lower sections 1902 and 1904 or walls include indentations 1902a, 1904a as positioning aids as described above. This may also be used as shown for a simple bite block without tongue stent but maintaining the open center for tongue positioning. IPD 1900 also includes handle or bar 1910 extending from middle section 1904 to enable a user to grasp IPD 1900. Handle 1910 may have various shapes to achieve desired results. Handle 1910 may incorporate ladder steps or ledges to add in grasping. Alternatively, handle 1910 may be open, solid or any other configuration to achieve desired results.

FIG. 23-27 depict views of another example IPD 2300 (intraoral positioning device). This IPD 2300 is similar to IPD 700 in FIGS. 7-12 (and other examples) in design and functionality. In that, IPD 2300 enables proper separation between the upper and lower arches of patient's mouth during treatment sessions. In this example, IPD 2300 includes a set of lower index ridges 2310 on the lower (bottom) section or wall which enable a patient to position his/her lower jaw to a finite position, i.e., to improve repeatability from planning through full treatment.

FIGS. 28-32 depict views of another example IPD 2800. IPD 2800 is configured to position and maintain a patient's tongue against the base of his/her mouth while creating separation between the upper and lower arches (jaws) of the patient's mouth. IPD 2800 comprises an engagement member 2801 that is configured to engage a patient's anatomical structures in his/her mouth including tissue, tongue and teeth as described below. Specifically, engagement member 2801 includes an (1) upper section or wall comprising inner segment 2802a, outer segment 2802b and transition segment 2802c between the inner and outer segments, (2) middle or side section or wall 2804 and a lower section or wall 2806.

Inner segment 2802a is constructed with a diameter sufficient to enable a patient to bite down for a treatment session. Outer segment 2802b has an arc shaped wall of generally singular diameter and it extends outwardly from the bottom of inner segment 2802a via a transition segment 2802c. However, outer segment 2802b curvature is opposite to the curvature of segment 2802a as shown. Because of this construction, transition segment 2802c has a steep slope from inner segment 2802a to outer segment 2802b, thereby essentially forming a wall of ninety-degrees in angle. Outer segment 2802b effectively extends directly from lower segment laterally. In this example, the tangential plane at the vertex (at the axis of symmetry) of the curvature of outer segment 2802b is parallel to the plane of handle 2810. Outer segment 2802b functions as a stent, thereby depressing a patient's tongue below IPD 2800. In other examples, outer segment 2802b may be constructed as flat or other shape to achieve desired results.

Inner segment 2802a includes an annular indentation or channel 2802a1 (as a positioning aid) positioned toward the rear of upper section 2802 for the maxilla or teeth to engage. Channel 2802a is defined by an annular shaped wall that is configured as a trough or groove. However, channel 2802a1 may be defined by two, three or more walls that create a groove. A wall may be linear or rounded to a degree. For example, channel 2802*a*1 may be configured as a rectangular groove. IPD 2800 further includes index ridges 2808 as describe above with respect to example IPD 2300. IPD 2800 further includes handle 2810 for grasping as described above.

FIGS. 33-37 depict views of another example IPD 3300. IPD 3300 is configured to position and maintain a patient's tongue laterally within his/her mouth while creating separation between the upper and lower arches (jaws) of the patient's mouth. IPD 3300 comprises engagement member 3301 for engaging anatomical structure in a patient's mouth including patient's tissue, tongue and teeth as described below. Engagement member 3301 includes a bite block that is defined by upper and lower sections or walls 3302, 3304, side sections or walls 3306, 3308 and front and back sections or walls 3310, 3312, respectively as shown. Upper and lower sections or walls 3302, 3304 are configured in an arc shape (concave) while side sections or walls 3302, 3304 and front and back sections or walls extend vertically to define shape of the bite block.

Figure 33:
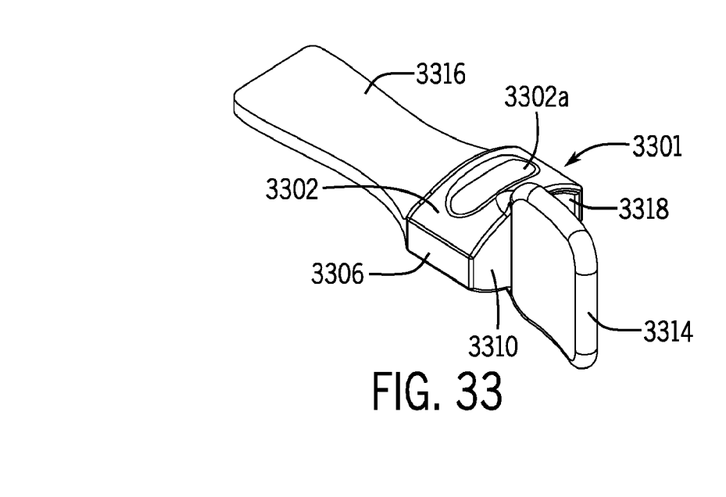
FIG. 33 depicts a front perspective view of another example IPD.
Figure 34:
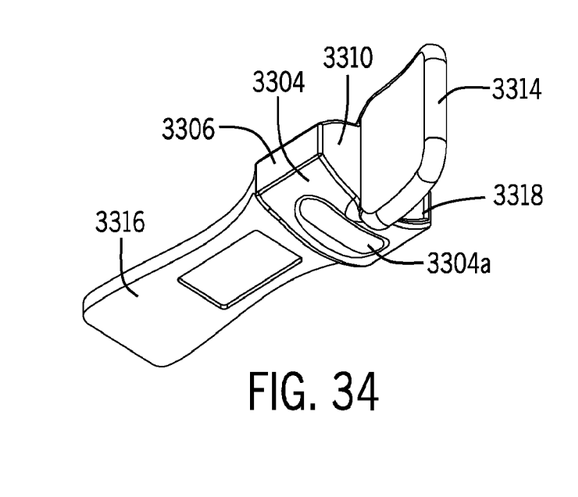
FIG. 34 depicts a bottom perspective view of the IPD in FIG. 33.
Figure 35:
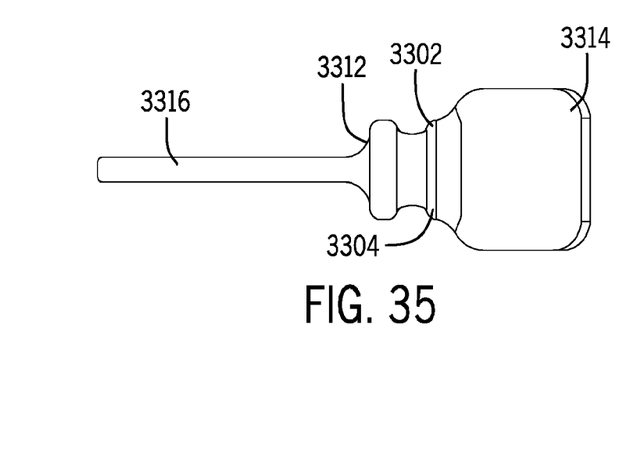
FIG. 35 depicts a side perspective view of the IPD in FIG. 33.
Figure 36:
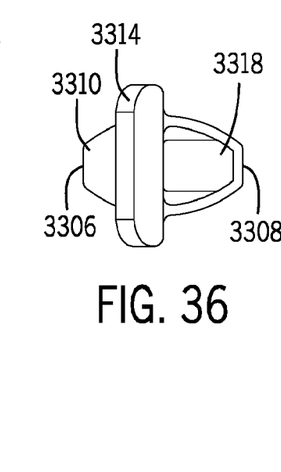
FIG. 36 depicts a front view of the IPD in FIG. 33.
Figure 37:
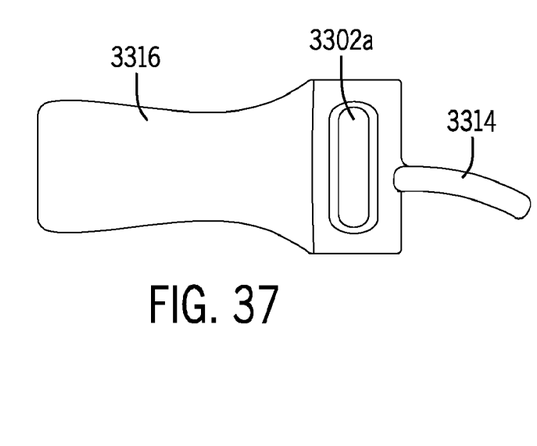
FIG. 37 depicts a top view of the IPD in FIG. 33.

As part of front section or wall 3310, the bite block includes opening 3318 to the right of stent 3314. Similar to the embodiments herein, opening 3318 is configured to receive a patient's tongue (i.e., a portion thereof) to stabilize the position of the patient's tongue. FIG. 36 best depicts wall 3310 including opening 3318.

Upper and lower sections 3302 and 3304 incorporate annular indentations or channels 3302*a* and 3304*a*, respectively (as positioning aids) for the maxilla, mandible or teeth (upper and lower) to engage. Engagement member 3301 further includes lateral displacement stent 3314 extending from front section 3310 of the bite block. Stent 3306 is configured vertically with respect to the axis of IPD 3300 and offset from the center of section 3310 as best shown in FIG. 36. Stent 3306 is configured to displace (move) a patient's tongue (left or right), i.e., cause the tongue to deviate in a desired direction. Stent 3306 is curved (diameter) to improve the patient's comfort during treatment.

As indicated, this stent (extended portion) 3314 acts as a displacement stent for the tongue, thereby limiting movement of the patient's tongue. Stent 3314 is configured as an arc (curved shape) as shown, but stent 3314 may be configured in any other shape to achieve desired results as known to those skilled in the art. A plane tangent at the vertex of the curvature shape of stent 3314 is vertical with respect to the plane of handle 3316 (as described below). In this example, the height of stent 3314 is greater than the height of front wall 3314 as shown. However, the dimensions of stent 3314 may vary as desired. Stent 3314 is offset from center of wall 3310 as shown, but it may be located at any position and angle to achieve desired results as known to those skilled in the art.

In this example, stent 3314, as best shown in FIG. 36, is configured to cause a patient's tongue to deviate to the right. However, IPD 3300 may be rotated 180 degrees to enable a practitioner to deploy IPD 3300 in a patient's mouth and cause a patient's tongue to deviate in the opposite direction (i.e., to the left).

IPD 3300 further includes handle 3316 extending from and attached to the engagement member 3301. The handle functions similar to those handles described above with respect to the other example IPDs.

For any example in this disclosure, an IPD may be constructed as an integral part or several parts constructed together (e.g., molding etc.). In addition, the material used to create the IPD may be plastic, photopolymer cured resins, composite plastics, ABS, ceramic, composite ceramic or any other suitable materials as known to those skilled in the arts. In addition, the material that the device is made of, as well as the general design may allow for radiation shielding/attenuation. Further, the IPD in these examples may be produced in different sizes to achieve a desired effect, typically a certain incisal opening or separation between the maxilla and mandible. The tongue positioning stent in the example in FIGS. 1-6 including the hollow cavity in the bite block (i.e., main body of the device) allow for the tongue to be positioned in a forward or elongated position with the main body of the tongue covered by the stent. The patient's tongue may be positioned differently as described above with the other examples in the figures.

It is to be understood that the disclosure teaches examples of the illustrative embodiments and that many variations of the invention can easily be devised by those skilled in the art after reading this disclosure and that the scope of the present invention is to be determined by the claim(s) below.

What is claimed is:

1. An intraoral positioning device (IPD) for positioning in a patient's mouth for radiation therapy planning and treatment, the device comprising:
    an engagement member configured to engage structure within a patient's mouth during radiation planning and/or treatment, wherein the engagement member includes an upper section, a lower section and a middle section extending from and between the upper and lower sections, whereby the upper, middle and lower sections together form walls of a bite block and define an opening for receiving and positioning a tongue of the patient, wherein the upper section is configured as an arc shape and the upper section includes an annular channel positioned toward a rear of the upper section and defined as a groove in the arc shape of the upper section for the maxilla or teeth of the patient to engage; and
    a handle extending from the engagement member to enable a user to grasp the IPD for introducing and removing it from the patient's mouth.

2. The IPD of claim 1 wherein the upper section has a portion that extends beyond the length of the lower section so as to function as a displacement stent for the patient's tongue, thereby limiting movement of the patient's tongue.

3. The IPD of claim 1 wherein the upper section defines an arc shape wall of a single diameter.

4. The IPD of claim 1 wherein the upper section includes an inner segment, an outer segment and a transition segment between the inner and outer segments, thereby transitioning between the inner and outer segments.

5. The IPD of claim 4 wherein the inner segment has a curvature shape having a first diameter and the outer segment has a curvature shape having a second diameter.

6. The IPD of claim 5 wherein the first and second diameters are different values.

7. The IPD of claim 5 wherein the transition segment has a curvature shape opposite to the curvature shape of the inner and outer segments.

8. An intraoral positioning device (IPD) for positioning in a patient's mouth for radiation therapy planning and treatment, the device comprising:
    an engagement member configured to engage structure within a patient's mouth during radiation planning or treatment, wherein the engagement member includes an upper wall, a lower wall and first and second side walls extending from and between the upper and lower walls, whereby the upper, lower and first and second side walls form top, bottom, front and rear walls of a bite block, wherein the upper wall is configured as an arc shape and the upper wall includes an annular channel positioned toward a rear of the upper wall and defined as a groove in the arc shape of the upper wall for the maxilla or teeth of the patient to engage; and a handle extending from the engagement member to enable a user to grasp the IPD for introducing and removing it from the patient's mouth.

9. The IPD of claim 8 further comprising a displacement stent extending from the first side wall.

10. The IPD of claim 9 wherein the displacement stent extends vertically with respect to the engagement member, thereby displacing a patient's tongue laterally.

11. The IPD of claim 9 wherein the displacement stent has a curved shape.

12. The IPD of claim 8 wherein the first side wall includes an opening for receiving a tongue of the patient.

* * * * *